(12) United States Patent
Kojima et al.

(10) Patent No.: US 11,690,594 B2
(45) Date of Patent: Jul. 4, 2023

(54) PIEZOELECTRIC ACTUATOR, ULTRASONIC ELEMENT, ULTRASONIC PROBE, ULTRASONIC DEVICE, AND ELECTRONIC DEVICE

(71) Applicant: Seiko Epson Corporation, Tokyo (JP)

(72) Inventors: Chikara Kojima, Matsumoto (JP); Koji Ohashi, Matsumoto (JP); Makoto Furuhata, Matsumoto (JP)

(73) Assignee: SEIKO EPSON CORPORATION

(*) Notice: Subject to any disclaimer, the term of this patent is extended or adjusted under 35 U.S.C. 154(b) by 0 days.

(21) Appl. No.: 17/454,879

(22) Filed: Nov. 15, 2021

(65) Prior Publication Data

US 2022/0151590 A1 May 19, 2022

(30) Foreign Application Priority Data

Nov. 16, 2020 (JP) .................. 2020-190124

(51) Int. Cl.
*A61B 8/00* (2006.01)
*G01N 29/24* (2006.01)
*H10N 30/20* (2023.01)

(52) U.S. Cl.
CPC .......... *A61B 8/4427* (2013.01); *A61B 8/4483* (2013.01); *A61B 8/4488* (2013.01); *A61B 8/4494* (2013.01); *G01N 29/2437* (2013.01); *H10N 30/2047* (2023.02)

(58) Field of Classification Search
CPC .................................................. B06B 1/0622
See application file for complete search history.

(56) References Cited

U.S. PATENT DOCUMENTS

| 2015/0258573 A1 | 9/2015 | Kojima |
| 2018/0078970 A1 | 3/2018 | Ono et al. |
| 2018/0192995 A1* | 7/2018 | Osawa ................. A61B 8/4494 |

FOREIGN PATENT DOCUMENTS

| JP | 4503423 B2 | 7/2010 |
| JP | 2015-188208 A | 10/2015 |
| JP | 2018-046512 A | 3/2018 |

* cited by examiner

*Primary Examiner* — Colin T. Sakamoto
*Assistant Examiner* — Tommy T Ly
(74) *Attorney, Agent, or Firm* — Harness, Dickey & Pierce, P.L.C.

(57) ABSTRACT

A piezoelectric actuator includes: a vibrating plate including a first surface configured to close an opening provided in a substrate and also including a second surface including a plurality of piezoelectric elements; a suppressing portion configured to suppress vibration of the vibrating plate; and a plurality of walls sticking out into the opening from the first surface, in which, when an active portion of a piezoelectric element is set as a portion where a first electrode, a piezoelectric layer, and a second electrode overlap, the walls are provided between adjacent active portions in plan view from a direction in which the first electrode, the piezoelectric layer, and the second electrode are stacked, and a distance between adjacent walls is longer than a distance between adjacent active portions in a plane perpendicular to the stacking direction.

10 Claims, 10 Drawing Sheets

PIEZOELECTRIC ACTUATOR, ULTRASONIC ELEMENT, ULTRASONIC PROBE, ULTRASONIC DEVICE, AND ELECTRONIC DEVICE

The present application is based on, and claims priority from JP Application Serial Number 2020-190124, filed on Nov. 16, 2020, the disclosure of which is hereby incorporated by reference herein in its entirety.

BACKGROUND

1. Technical Field

The present disclosure relates to a piezoelectric actuator, an ultrasonic element, an ultrasonic probe, an ultrasonic device, and an electronic device.

2. Related Art

As disclosed in JP-A-2015-188208, there is known an ultrasonic wave sensor. The ultrasonic wave sensor includes a substrate in which an opening is formed, a vibrating plate provided at the substrate so as to close the opening, and a plurality of piezoelectric elements including a first electrode, a piezoelectric layer, and a second electrode each stacked at an opposite side of the vibrating plate from the opening. In the ultrasonic wave sensor, an active portion is set as a portion where the first electrode, the piezoelectric layer, and the second electrode completely overlap in a direction in which the first electrode, the piezoelectric layer, and the second electrode are stacked. A suppressing portion configured to suppress vibration of the vibrating plate is provided between adjacent active portions.

With the configuration described above, it is possible to increase the size of the opening relative to the active portion. However, when the size of the opening is increased, there is a possibility that this brings a state in which the vibrating plate or the like can be directly touched from the outside, which may lead to a malfunction. By providing a beam at the opening, it is possible to protect the vibrating plate or the like from the outside. However, this causes a problem in that vibration of the vibrating plate is transferred to the beam to vibrate the beam, which generates vibration at unwanted frequencies.

SUMMARY

A piezoelectric actuator includes a substrate in which an opening is formed, a vibrating plate provided at the substrate and having a first surface configured to close the opening, a plurality of piezoelectric elements provided at a second surface correspondingly to the opening, the second surface being at an opposite side of the vibrating plate from the first surface, a suppressing portion provided correspondingly to the piezoelectric elements and configured to suppress vibration of the vibrating plate, and a plurality of walls sticking out into the opening from the first surface, in which the piezoelectric elements include a first electrode, a piezoelectric layer, and a second electrode stacked in this order from a side of the second surface, when an active portion is set as a portion where the first electrode, the piezoelectric layer, and the second electrode overlap, the wall is provided between the active portions adjacent to each other in plan view from a stacking direction, and a distance between the walls adjacent to each other is longer than a distance between the active portions adjacent to each other in a plane perpendicular to the stacking direction.

An ultrasonic element includes the piezoelectric actuator described above, a transmission circuit configured to cause the piezoelectric actuator to transmit an ultrasonic wave, and a reception circuit configured to cause the piezoelectric actuator to receive an ultrasonic wave.

An ultrasonic probe includes the ultrasonic element described above, and a housing configured to accommodate the ultrasonic element.

An ultrasonic device includes the ultrasonic element described above, and a controller configured to control the ultrasonic element.

An electronic device includes the piezoelectric actuator described above.

DESCRIPTION OF EXEMPLARY EMBODIMENTS

1. First Embodiment

An ultrasonic measurement device 1 according to a first embodiment will be described with reference to FIGS. 1 and 2.

Figure 1:
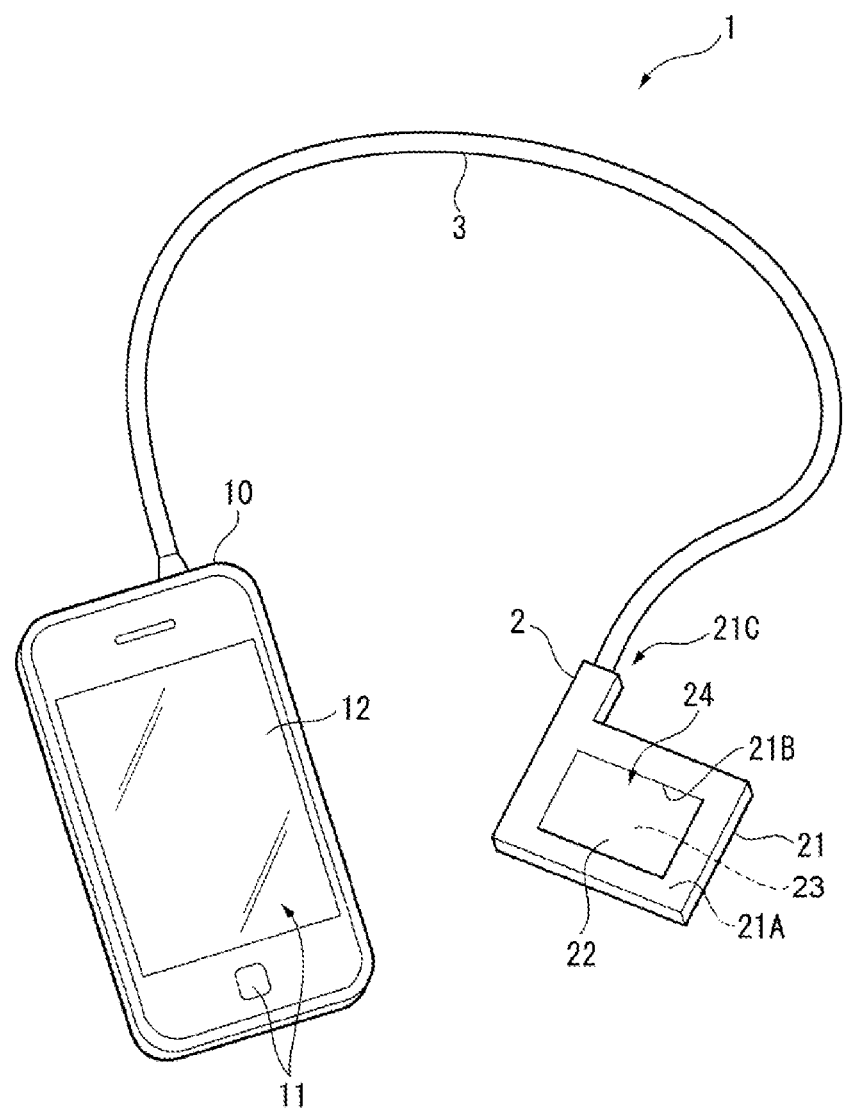
FIG. 1 is a perspective view illustrating a schematic configuration of an ultrasonic measurement device according to a first embodiment.
Figure 2:
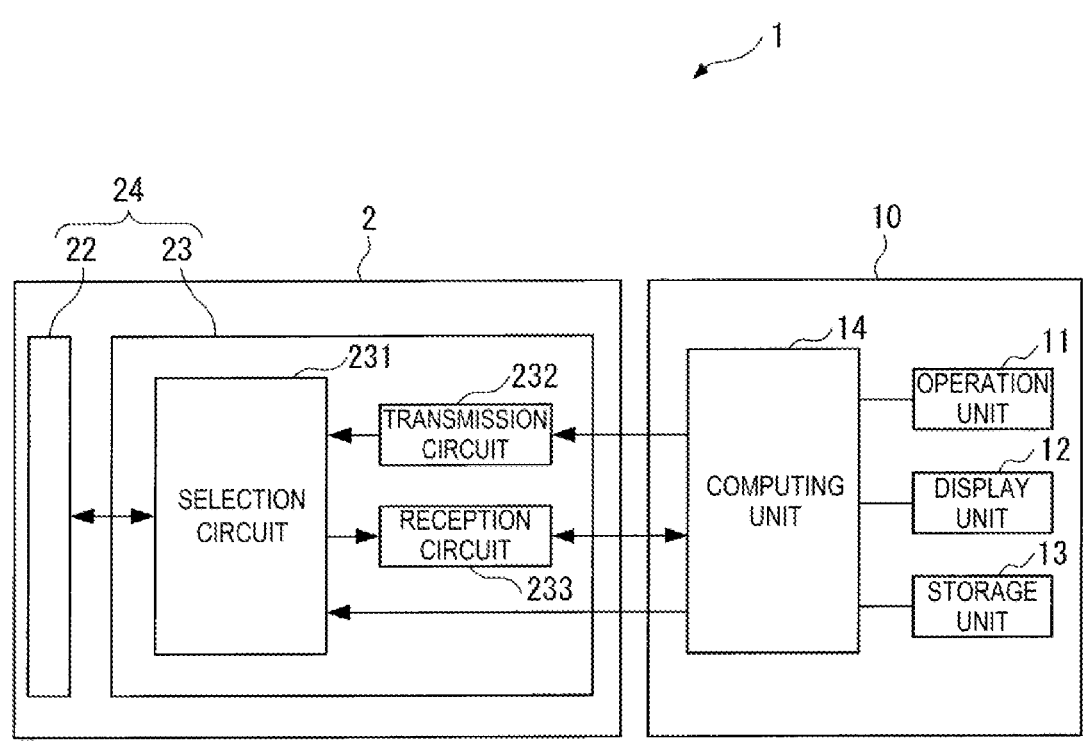
FIG. 2 is a block diagram illustrating a schematic configuration of the ultrasonic measurement device according to the first embodiment.

The ultrasonic measurement device 1, which serves as an ultrasonic device and an electronic device according to the present embodiment, includes an ultrasonic probe 2 and a controller 10 electrically coupled to the ultrasonic probe 2 through a cable 3, as illustrated in FIGS. 1 and 2.

With the ultrasonic measurement device 1, the ultrasonic probe 2 is brought into contact with a front surface of a living body such as a human body to deliver an ultrasonic wave from the ultrasonic probe 2. The ultrasonic wave reflected within the living body is received by the ultrasonic probe 2. On the basis of the reception signal, it is possible to acquire an endosonographic image of the inside of the living body or measure a state of organs within the living body such as blood flow.

The ultrasonic probe 2 includes an ultrasonic element 24 and a housing 21 configured to accommodate the ultrasonic element 24.

The ultrasonic element 24 includes a piezoelectric actuator 22, and a printed wired board 23 configured to control the piezoelectric actuator 22.

The printed wired board 23 includes: a transmission circuit 232 used to transmit an ultrasonic wave from the piezoelectric actuator 22; a reception circuit 233 used to cause the piezoelectric actuator 22 to receive the ultrasonic wave to output a reception signal; and a selection circuit 231.

On the basis of control by the controller 10, the selection circuit 231 switches between transmission coupling and reception coupling. In the transmission coupling, the piezoelectric actuator 22 and the transmission circuit 232 are coupled. In the reception coupling, the piezoelectric actuator 22 and the reception circuit 233 are coupled.

When switching is made into the transmission coupling, the transmission circuit 232 outputs a transmission signal used to transmit an ultrasonic wave, through the selection circuit 231 to the piezoelectric actuator 22.

When switching is made into the reception coupling, the reception circuit 233 outputs, to the controller 10, a reception signal inputted from the piezoelectric actuator 22 through the selection circuit 231. The reception circuit 233 converts the reception signal into a digital signal, removes a noise component, and performs various signal processing such as amplification to obtain a desired signal level. Then, the reception circuit 233 outputs, to the controller 10, the reception signal after the processing.

The housing 21 is formed, for example, into a rectangular box shape. One face of the housing 21 serves as a sensor surface 21A, and a sensor window 21B is provided in the sensor surface 21A. A portion of the piezoelectric actuator 22 is exposed from the sensor window 21B. In addition, a path hole 21C for the cable 3 is provided in a portion of the housing 21. The cable 3 is coupled from the path hole 21C to the printed wired board 23.

The controller 10 includes an operation unit 11, a display unit 12, a storage unit 13, and a computing unit 14. The controller 10 controls the ultrasonic element 24. For the controller 10, it is possible to use, for example, a general purpose terminal device such as a smartphone or a personal computer, or a dedicated terminal device used to operate the ultrasonic probe 2.

The operation unit 11 is a user interface used to operate the ultrasonic measurement device 1, and it is possible to use, for example, a touch screen or an operation button or the like provided on the display unit 12. The display unit 12 is comprised, for example, of a liquid crystal display or the like, and causes an image to be displayed. The storage unit 13 holds various types of programs and various types of data used to control the ultrasonic measurement device 1. The computing unit 14 is comprised, for example, of a computation circuit such as a CPU or a storage circuit such as a memory. The computing unit 14 reads and executes various types of programs held in the storage unit 13 to control, for the transmission circuit 232, the generation or the output process of a transmission signal, an control, for the reception circuit 233, the frequency setting or gain setting or the like of a reception signal.

The piezoelectric actuator 22 according to the first embodiment will be described with reference to FIGS. 3 to 6, and FIG. 9. Note that FIG. 5 illustrates a state in which a seal panel 42 is removed, for the purpose of convenience of explaining the configuration of the inside of the piezoelectric actuator 22. In addition, in the drawings, the dimensional proportion of individual constituent elements differ from the actual proportions, for the purpose of convenience of explanation.

As for the coordinates attached to the drawings, description will be made such that three axes perpendicular to each other are set as an X-axis, a Y-axis, and a Z-axis. The direction extending along the X-axis is set as an "X direction", the direction extending along the Y-axis is set as a "Y direction", and the direction extending along the Z-axis is set as a "Z direction". The direction of the arrow is set as a plus direction. In addition, description will be made on the assumption that, in plan view from the Z direction, the surface disposed at the Z-direction plus side is set as an upper surface, and the surface disposed at the Z-direction minus side, which is an opposite side from the Z-direction plus side, is set as a lower surface.

Figure 3:
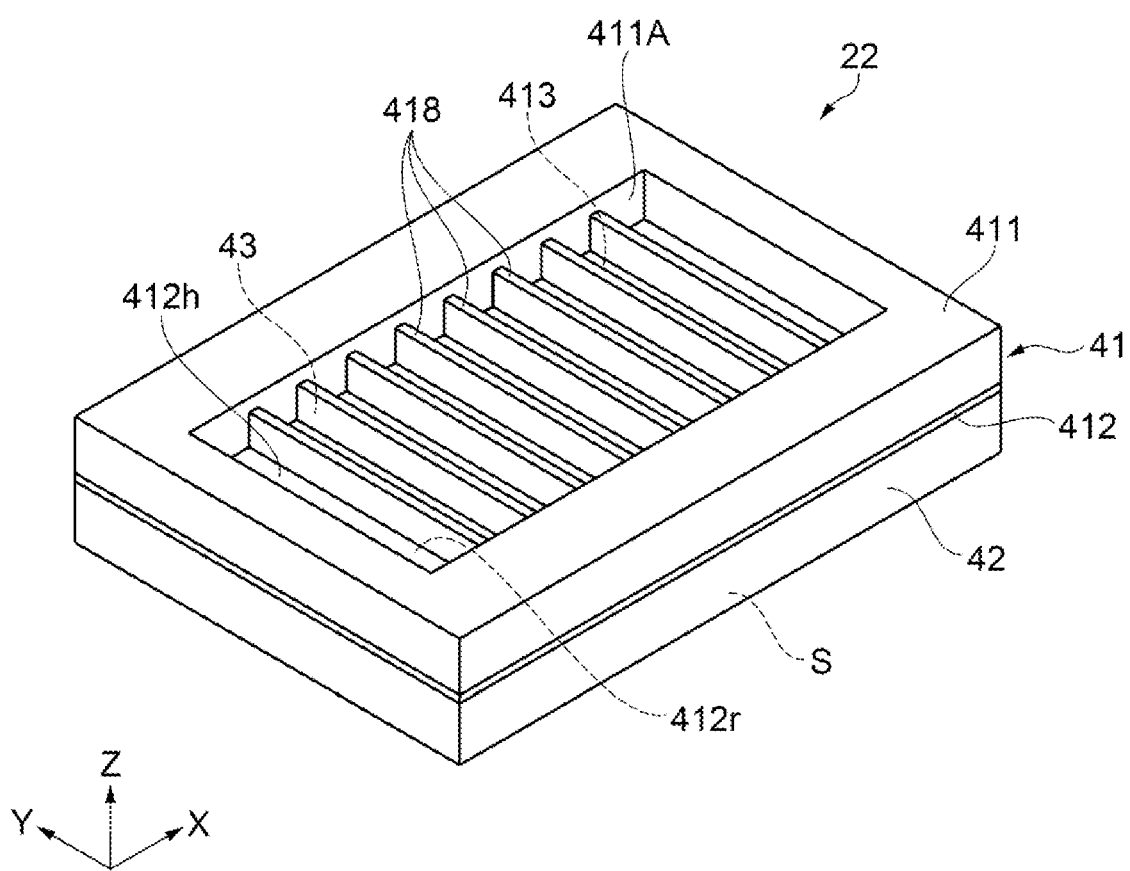
FIG. 3 is a perspective view illustrating a schematic configuration of a piezoelectric actuator according to the first embodiment.

As illustrated in FIG. 3, the piezoelectric actuator 22 includes a base portion 41, the seal panel 42, and a suppressing portion 43.

Figure 4:
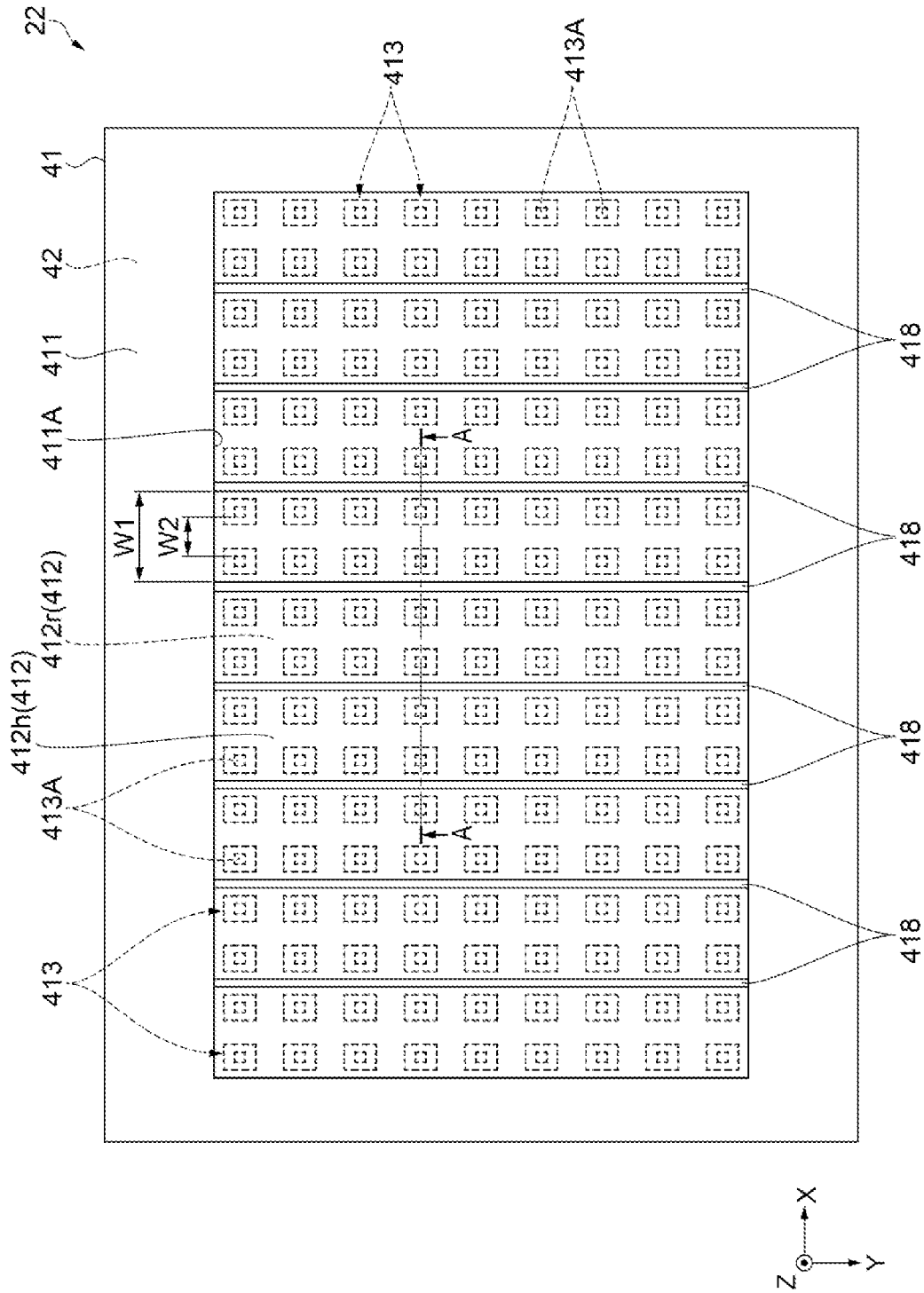
FIG. 4 is a plan view illustrating a piezoelectric actuator according to the first embodiment as viewed from a base portion side.
Figure 5:
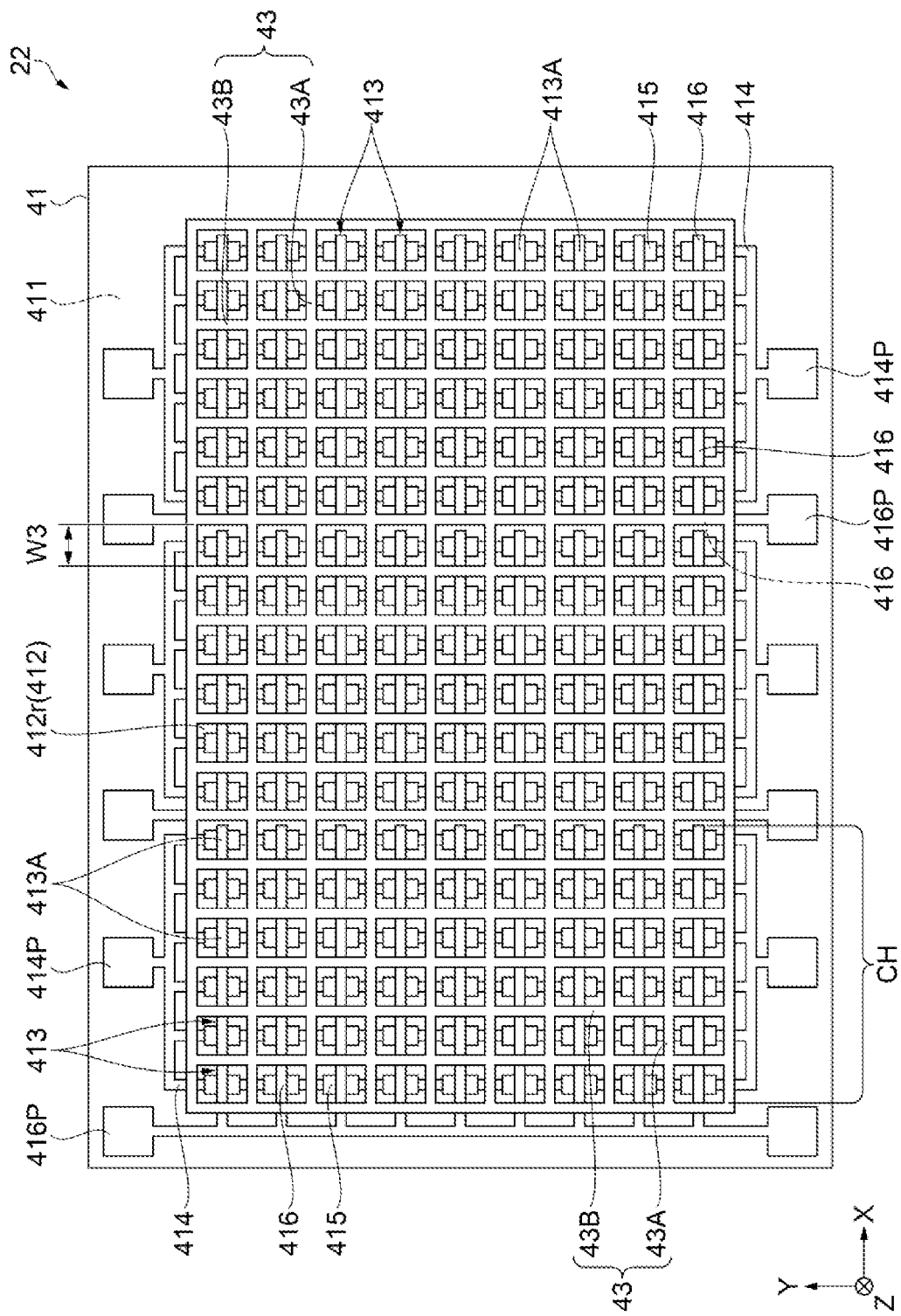
FIG. 5 is a plan view illustrating the piezoelectric actuator according to the first embodiment as viewed from a seal panel side.

As illustrated in FIGS. 3 and 4, the base portion 41 includes: a substrate 411 in which an opening 411A is formed; a vibrating plate 412 configured to close the opening 411A; a plurality of piezoelectric elements 413 provided at the vibrating plate 412; and a plurality of walls 418 provided at the vibrating plate 412. Note that an acoustic matching layer or acoustic lens or the like may be provided at the opening 411A of the substrate 411.

The substrate 411 is a semiconductor substrate made out of silicon or the like. The substrate 411 includes the opening 411A at the central portion of the substrate 411 in plan view from the Z direction. In the present embodiment, the opening 411A has a rectangular shape in which the lengths of sides parallel to the Y direction are shorter than the lengths of sides parallel to the X direction in plan view from the Z direction.

For example, the vibrating plate 412 is a thin membrane made of silicon oxide or is comprised of a stacked body or the like made out of silicon oxide and zirconium oxide. The vibrating plate 412 includes a first surface 412h and a second surface 412r disposed at an opposite side from the first surface 412h. The first surface 412h constitutes an upper surface of the vibrating plate 412, and the second surface 412r constitutes a lower surface of the vibrating plate 412. The vibrating plate 412 is provided at a lower surface of the substrate 411, and the first surface 412h of the vibrating plate 412 closes the opening 411A of the substrate 411 from the lower face side of the substrate 411.

The walls 418 are provided at the first surface 412h of the vibrating plate 412, and stick out into the opening 411A from the first surface 412h. With the walls 418 being provided, it is possible to prevent the vibrating plate 412 from being directly touched from the outside through the opening 411A.

The walls 418 extend in parallel to the Y direction in plan view from the Z direction. In addition, the walls 418 each have end portions at the Y-direction plus side and the Y-direction minus side each coupled to the peripheral edges of the Y-direction plus side and the Y-direction minus side of the opening 411A. This enables the walls 418 to function as a beam for supporting the vibrating plate 412, which makes it possible to improve the strength of the vibrating plate 412.

Note that, in the present embodiment, as described above, the opening 411A has a rectangular shape in which, in plan view from the Z direction, the lengths of sides parallel to the Y direction are smaller than the length of sides parallel to the X direction. Thus, in a case where the walls 418 extend in parallel to the Y direction that is the shorter-side direction of the opening 411A, the lengths of the walls 418 are shorter, as compared with a case where the walls 418 extend in parallel to the X direction that is the longitudinal direction of the opening 411A. For this reason, by causing the walls 418 to extend in parallel to the Y direction, it is possible to increase the strength of the walls 418.

In the present embodiment, the walls 418 are formed by applying patterning on the substrate 411 using a photolithography technique. However, the formation is not limited to this. For example, it may be possible to form it with a resin material by applying a photosensitive resin material on the opening 411A using spin coating or sputtering or the like, and then performing patterning using a photolithography technique.

The piezoelectric elements 413 and the suppressing portion 43 are provided at the second surface 412r of the vibrating plate 412.

The seal panel 42 is formed so as to have substantially the same shape as the substrate 411 in plan view from the Z direction. The seal panel 42 is disposed so as to be opposed to the second surface 412r of the vibrating plate 412. The upper surface of the seal panel 42 and the lower surface of the substrate 411 are joined to each other with the vibrating plate 412 being interposed therebetween. The seal panel 42 has a space S comprised of a recessed portion obtained by making the central portion, in plan view from the Z direction, of the upper surface recessed downward. The piezoelectric elements 413 provided at the second surface 412r of the vibrating plate 412 are sealed in this space S.

Figure 6:
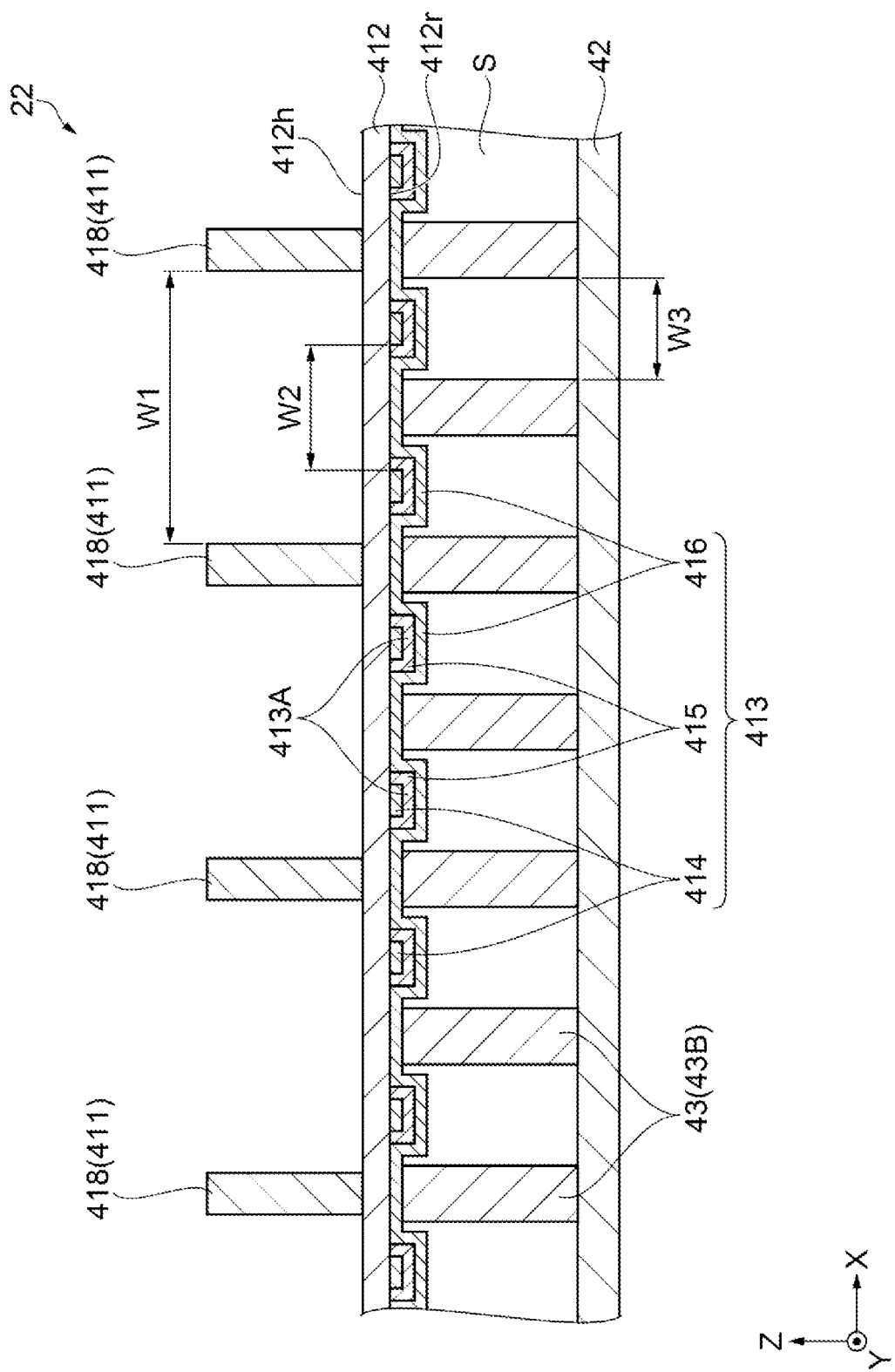
FIG. 6 is a cross-sectional view taken along the line A-A in FIG. 4.

As illustrated in FIGS. 4 to 6, the plurality of piezoelectric elements 413 are provided at the second surface 412r disposed at the opposite side of the vibrating plate 412 from the first surface 412h correspondingly to the opening 411A of the substrate 411. Specifically, the piezoelectric elements 413 are disposed so as to overlap with the opening 411A in plan view from the Z direction.

The piezoelectric element 413 are stacked bodies in which the first electrode 414, the piezoelectric layer 415, and the second electrode 416 are stacked. The first electrode 414, the piezoelectric layer 415, and the second electrode 416 are stacked in the order of the first electrode 414, the piezoelectric layer 415, and the second electrode 416 from the second surface 412r side of the vibrating plate 412. A portion where the first electrode 414, the piezoelectric layer 415, and the second electrode 416 overlap in plan view from the Z direction serves as an active portion 413A. The Z direction is a direction of stacking in which the first electrode 414, the piezoelectric layer 415, and the second electrode 416 are stacked.

The first electrode 414 is provided so as to extend in the Y direction and continue over the plurality of active portions 413A. End portions, at the Y-direction plus side and the Y-direction minus side, of the plurality of first electrodes 414 arranged in the X direction are coupled to each other at the outer peripheral edges, at the Y-direction plus side and the Y-direction minus side, of the substrate 411, and are also electrically coupled to a first electrode terminal 414P provided at the outer peripheral edge, at the Y-direction plus side and the Y-direction minus side, of the substrate 411.

The piezoelectric layer 415 is disposed in a matrix manner correspondingly to an intersecting position of the first electrode 414 and the second electrode 416 in plan view from the Z direction. For the piezoelectric layer 415, it is possible to typically use composite oxide having a lead zirconate titanate-based perovskite structure. This makes it possible to easily obtain the amount of displacement of the piezoelectric elements 413. In addition, for the piezoelectric layer 415, it is also possible to use composite oxide having a perovskite structure that does not contain lead. This makes it possible to achieve a piezoelectric actuator 22 by using a non-lead-based material that has less impact on the environment.

The second electrode 416 is provided so as to extend in the X direction and continue over the plurality of active portions 413A. End portions, at the X-direction minus side, of the plurality of second electrodes 416 arranged in the Y direction are coupled to each other, and are drawn to the outer peripheral edges, at the Y-direction plus side and the Y-direction minus side, of the substrate 411. The second electrodes 416 drawn to the outer peripheral edges of the substrate 411 are electrically coupled to a second electrode terminal 416P provided at the outer peripheral edges, at the Y-direction plus side and the Y-direction minus side, of the substrate 411.

Any material can be used for the first electrode 414 or the second electrode 416, provided that the material has an electrically conductive property. For the material of the first electrode 414 or the second electrode 416, it is possible to use an electrically conductive layer made, for example, of iridium, platinum, or titanium. Note that the electrically conductive layer may be a single layer or multiple layers.

The plurality of piezoelectric elements 413 are arranged along the Y direction and the X direction in a matrix manner. The Y direction extends along the Y-axis that is a first axis perpendicular to the Z direction that is a direction of stacking in which the first electrode 414, the piezoelectric layer 415, and the second electrode 416 are stacked in the active portion 413A. The X direction extends along the X-axis that is a second axis perpendicular to the Y-axis that is the first axis. In the present embodiment, one transmission-reception line is formed by a plurality of piezoelectric elements 413 arranged in one line in the Y direction. In addition, one channel CH is formed by plural lines of transmission-reception line arranged along the X direction. Furthermore, a matrix of a plurality of piezoelectric elements 413 is formed by a plurality of channels CH arranged along the X direction.

As illustrated in FIGS. 5 and 6, the suppressing portion 43 is provided at the second surface 412r of the vibrating plate 412. The upper surface of the suppressing portion 43 is joined to the second surface 412r of the vibrating plate 412. The lower surface of the suppressing portion 43 is joined to the seal panel 42. In this manner, the suppressing portion 43 fixes the vibrating plate 412, which makes it possible to suppress the vibration of the vibrating plate 412.

The suppressing portion 43 is provided correspondingly to the piezoelectric element 413. The suppressing portion 43 includes a plurality of first suppressing portions 43A formed so as to extend in the X direction, and a plurality of second suppressing portions 43B formed so as to extend in the Y direction. The first suppressing portions 43A are each disposed between piezoelectric elements 413 adjacent to each other in the Y direction. The second suppressing portions 43B are each disposed between piezoelectric elements 413 adjacent to each other in the X direction. That is, at the vibrating plate 412, a first suppressing portion 43A is disposed at the Y-direction plus side and the Y-direction minus side of the piezoelectric element 413. In addition, at the vibrating plate 412, a second suppressing portion 43B is disposed at the X-direction plus side and the X-direction minus side of the piezoelectric element 413. In this manner, the suppressing portion 43 can restrict the vibrating area in the Y direction and the X direction of the vibrating plate 412.

The suppressing portion 43 is made, for example, of a resin material, and can be formed by applying a photosensitive resin material on the vibrating plate 412 using spin coating or sputtering or the like, and then performing patterning using a photolithography technique.

Note that, as described above, in the present embodiment, the suppressing portion 43 is provided at the second surface 412*r* of the vibrating plate 412. However, the suppressing portion 43 may be provided at the first surface 412*h* of the vibrating plate 412. However, when the suppressing portion 43 is provided at the second surface 412*r* of the vibrating plate 412, it is possible to more easily suppress the vibration of the vibrating plate 412.

The seal panel 42 includes not-illustrated through holes disposed at positions that correspond to the first electrode terminal 414P and the second electrode terminal 416P in plan view from the Z direction. For example, a not-illustrated wiring member such as a flexible printed circuit (FPC) is inserted through the not-illustrated through hole. Through this not-illustrated wiring member, the first electrode terminal 414P and the second electrode terminal 416P are electrically coupled to the printed wired board 23.

At the time of transmitting an ultrasonic wave, a drive signal is inputted from the printed wired board 23 to the first electrode terminal 414P through the wiring member, and a common bias signal is inputted to the second electrode terminal 416P. By controlling the signal intensity or the signal input timing of the drive signal inputted to the first electrode terminal 414P, a difference in potential occurs between the first electrode 414 of the active portion 413A and the second electrode 416 to vibrate the piezoelectric layer 415. This cause the vibrating plate 412 to vibrate to generate an ultrasonic wave.

At the time of receiving an ultrasonic wave, a common bias signal is inputted from the printed wired board 23 to the second electrode terminal 416P. In addition, an ultrasonic wave coming from a target object is inputted from the piezoelectric actuator 22. Upon the vibrating plate 412 vibrating, the piezoelectric element 413 deflects. In response to the deflection of the piezoelectric element 413, a difference in potential occurs between the first electrode 414 and the second electrode 416. Thus, a detection signal corresponding to the ultrasonic wave from the target object is outputted from the first electrode terminal 414P to the printed wired board 23.

As illustrated in FIGS. 4 and 6, a plurality of walls 418 that stick out into the opening 411A from the first surface 412*h* are provided at the first surface 412*h* of the vibrating plate 412. With the walls 418, the opening 411A is partitioned into a plurality of small openings. In other words, the walls 418 function as partitions that surround the plurality of small openings.

The plurality of walls 418 are provided between active portions 413A disposed adjacent to each other in plan view from the Z direction that is a direction of stacking in which the first electrode 414, the piezoelectric layer 415, and the second electrode 416 are stacked in the active portion 413A of the piezoelectric element 413. The plurality of walls 418 extend parallel to the Y direction extending along the Y-axis that is the first axis perpendicular to the Z direction. The plurality of walls 418 extending parallel to the Y direction are arranged along the X direction extending along the X-axis that is the second axis perpendicular to the Y-axis that is the first axis.

Note that, in the present embodiment, the walls 418 extend parallel to the Y direction. However, the walls 418 may extend parallel to the X direction.

As illustrated in FIGS. 4 to 6, the walls 418 and the active portions 413A are disposed in a manner such that the distance W1 between walls 418 disposed adjacent to each other along the X direction is longer than the distance W2 between active portions 413A of the piezoelectric elements 413 disposed adjacent to each other along the X direction. By increasing the distance W1 between walls 418 disposed adjacent to each other along the X direction as described above, it is possible to weaken the connection between walls 418. This makes it possible to suppress generation of vibration at unwanted frequencies.

Furthermore, the walls 418 and the suppressing portions 43 are disposed in a manner such that the distance W1 between walls 418 disposed adjacent to each other along the X direction is at least twice the distance W3 between suppressing portions 43 disposed adjacent to each other along the X direction. The distance W3 between suppressing portions 43 disposed adjacent to each other along the X direction indicates the width, in the X direction, of a vibration region where the vibrating plate 412 can vibrate with the vibration of the active portion 413A without being suppressed by the suppressing portion 43. That is, by disposing the walls 418 and the suppressing portions 43 in a manner such that the distance W1 between walls 418 disposed adjacent to each other along the X direction is at least twice the distance W3 between suppressing portions 43 disposed adjacent to each other along the X direction, it is possible to arrange, in the X direction, two or more vibration regions where the vibrating plate 412 can vibrate without being suppressed by the suppressing portion 43, the vibration regions being disposed between walls 418 disposed adjacent to each other along the X direction. In the present embodiment, two vibration regions are arranged in the X direction and between walls 418 disposed adjacent to each other along the X direction, the two vibration regions being regions where the vibrating plate 412 can vibrate without being suppressed by the suppressing portion 43.

In this manner, the distance W1 between walls 418 disposed adjacent to each other along the X direction is at least twice the distance W3 between suppressing portions 43 disposed adjacent to each other along the X direction. This makes it possible to reduce the number of walls 418 to which the vibration of the vibrating plate 412 is transferred. Thus, it is possible to weaken the connection between the walls 418, which makes it possible to suppress the generation of vibration at unwanted frequencies.

In addition, in the present embodiment, a plurality of active portions 413A are disposed along the X direction and between walls 418 disposed adjacent to each other along the X direction. Specifically, two active portions 413A are disposed along the X direction and between walls 418 disposed adjacent to each other along the X direction. Note that the number of active portions 413A disposed along the X direction and between walls 418 disposed adjacent to each other along the X direction is any number, provided that the number is more than or equal to two.

Here, an effect of the distance W1 between adjacent walls 418 on the piezoelectric actuator 22 will be described by comparing the present embodiment and a comparative example.

First, a piezoelectric actuator 22A according to a comparative example will be described with reference to FIG. 7.

Figure 7:
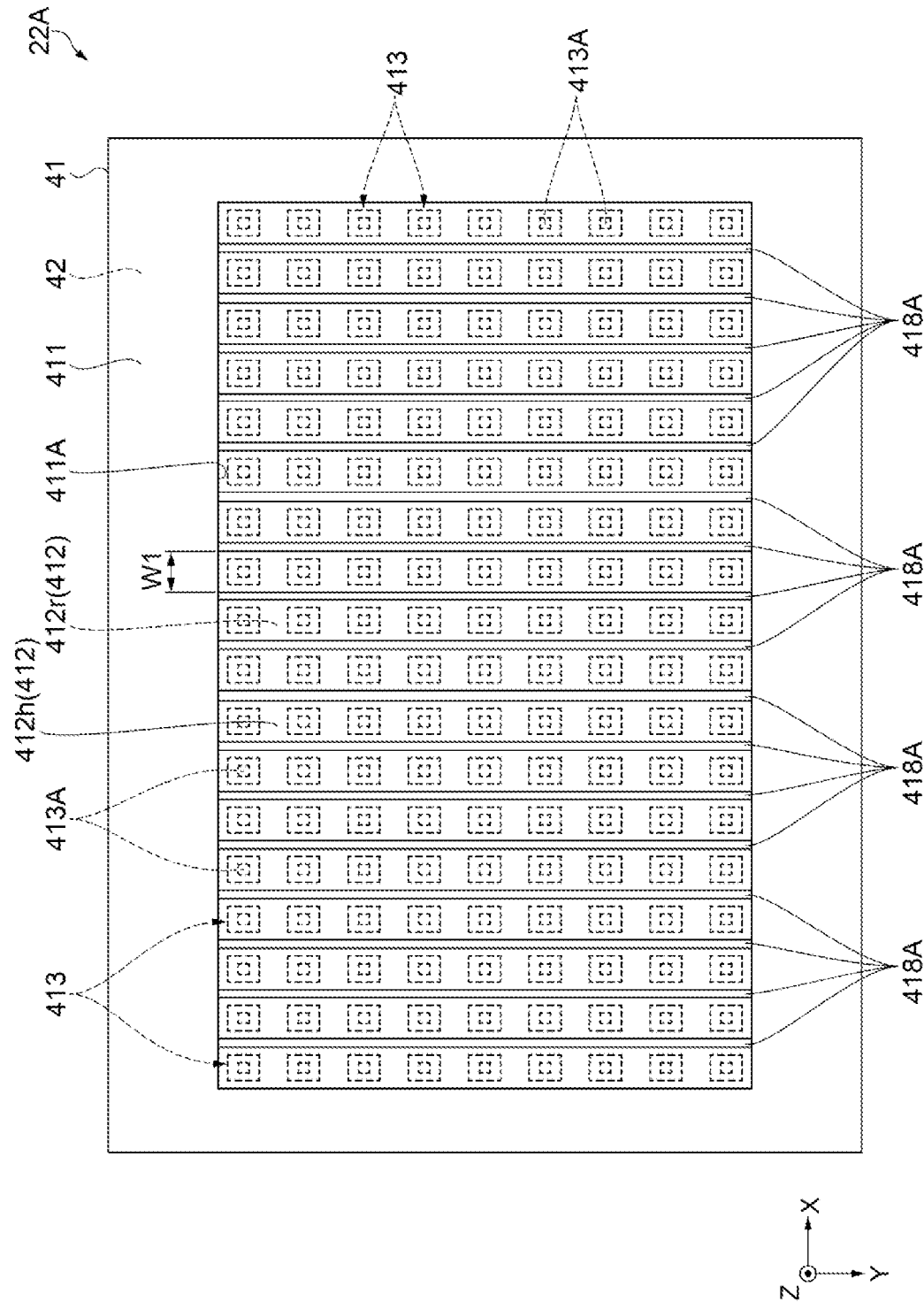
FIG. 7 is a plan view illustrating a piezoelectric actuator according to a comparative example as viewed from a base portion side.

As illustrated in FIG. 7, in the piezoelectric actuator 22A according to the comparative example, a distance W1 between adjacent walls 418A is smaller than that of the piezoelectric actuator 22 according to the present embodiment, and one piezoelectric element 413 is disposed between walls 418A disposed adjacent to each other along the X direction.

Next, with reference to FIGS. 8 and 9, a frequency spectrum will be described as to the piezoelectric actuator 22A according to the comparative example and the piezoelectric actuator 22 according to the present embodiment. Note that the frequency spectrum indicates which frequency is included in the vibration to be measured and how strong it is.

Figure 8:
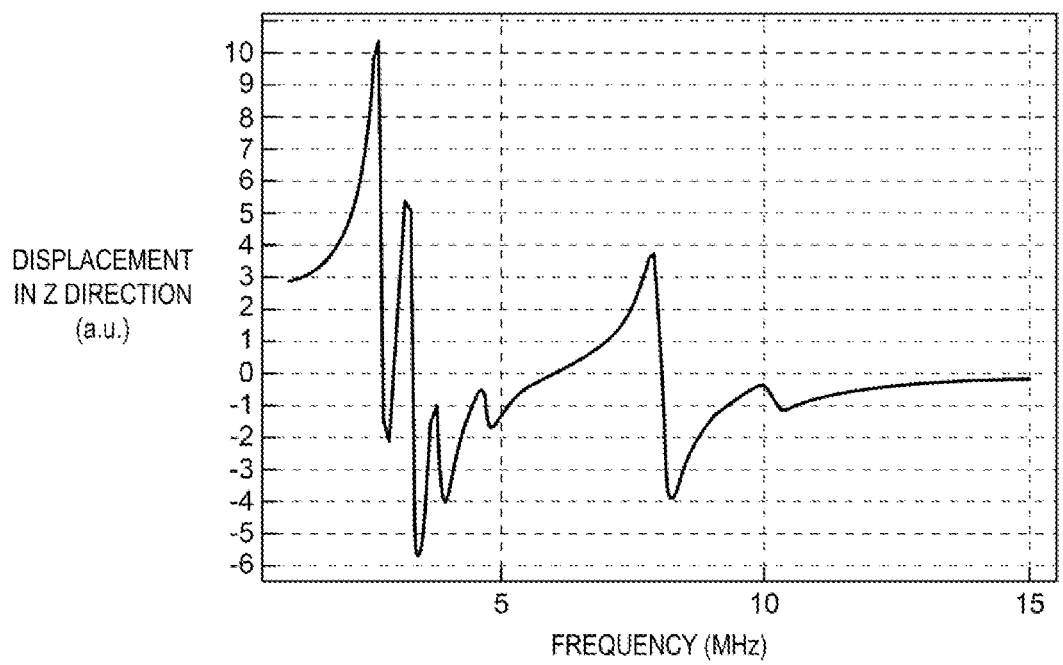
FIG. 8 is a diagram illustrating a frequency spectrum of the piezoelectric actuator according to the comparative example.

As illustrated in FIG. 8, the frequency spectrum of the piezoelectric actuator 22A according to the comparative example exhibits that the intensity at 3 to 4 MHz, which are desired frequencies, is high and vibration at other frequencies, which are unwanted frequencies, also has a high intensity. This is because, in the piezoelectric actuator 22A, the distance W1 between adjacent walls 418A is small as described above. Thus, the vibration at the vibrating plate 412 is transferred to walls 418A to cause the walls 418A to vibrate. Upon the walls 418A vibrating, the vibrations at the walls 418A are connected between the adjacent walls 418A. Thus, the walls 418A are more likely to produce resonance.

Figure 9:
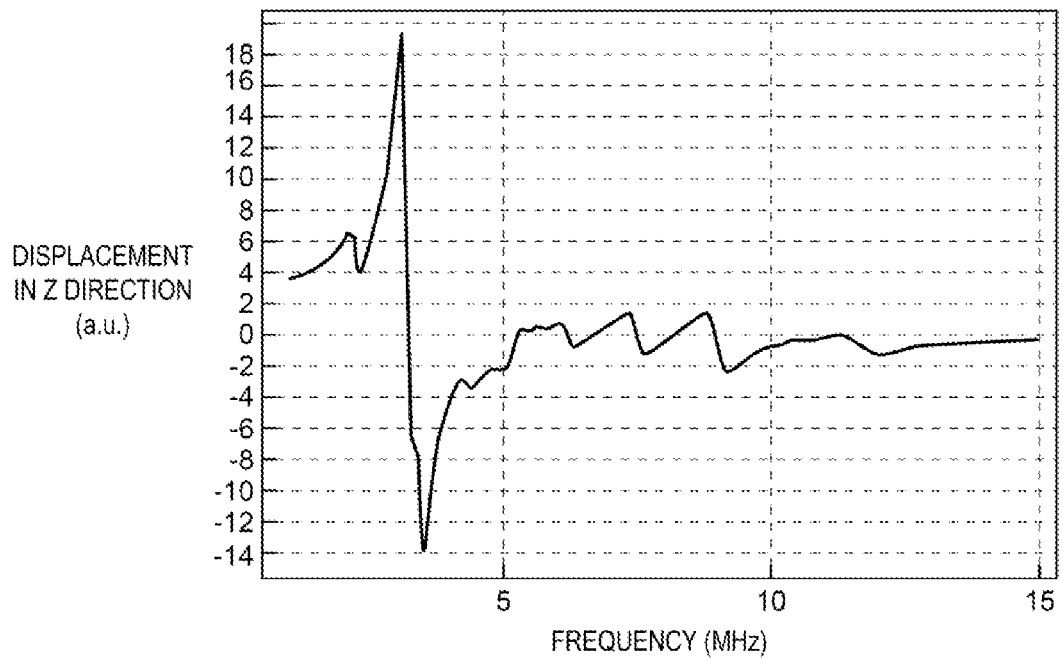
FIG. 9 is a diagram illustrating a frequency spectrum of the piezoelectric actuator according to the first embodiment.

In contrast, in a case of the frequency spectrum of the piezoelectric actuator 22 according to the present embodiment, the intensity at 3 to 4 MHz, which are desired frequencies, is much higher than that of the piezoelectric actuator 22A according to the comparative example, and the intensity of vibration at other unwanted frequencies is low, as illustrated in FIG. 9. As described above, in the present embodiment, the distance W1 between walls 418 disposed adjacent to each other along the X direction is large, and the distance W1 between walls 418 disposed adjacent to each other along the X direction is set to be longer than the distance W2 between active portions 413A of piezoelectric elements 413 disposed adjacent to each other along the X direction. Thus, when vibration of the vibrating plate 412 is transferred to walls 418 to cause the walls 418 to vibrate, vibrations of the walls 418 are less likely to be connected between adjacent walls 418. This makes it possible to suppress the generation of vibration at unwanted frequencies due to resonance of the walls 418.

Note that, in the present embodiment, a plurality of walls 418 extend parallel to the Y direction perpendicular to the Z direction, and are arranged along the X direction. However, a plurality of walls 418 may extend parallel to the X direction perpendicular to the Z direction, and be arranged along the Y direction. The direction along which the walls 418 are arranged is not limited to the Y direction extending along the Y-axis that is the second axis. Even when walls 418 are arranged along the X direction extending along the X-axis serving as the first axis, it is possible to obtain an effect similar to that of the present embodiment, by disposing walls 418 and active portions 413A in a manner such that the distance W1 between adjacent walls 418 is longer than the distance W2 between adjacent active portions 413A in an X-Y plane that is a plane including the Y-axis serving as the first axis perpendicular to the Z-axis and also including the X-axis serving as the second axis.

As described above, with the present embodiment, it is possible to obtain the following effects.

The piezoelectric actuator 22 includes: the vibrating plate 412 including the first surface 412h configured to close the opening 411A provided in the substrate 411 and also including the second surface 412r provided with the plurality of piezoelectric elements 413; the suppressing portion 43 configured to suppress vibration of the vibrating plate 412; and the plurality of walls 418 sticking out into the opening 411A from the first surface 412h. When the active portion 413A of the piezoelectric element 413 is set as a portion where the first electrode 414, the piezoelectric layer 415, and the second electrode 416 overlap, the wall 418 is provided between adjacent active portions 413A in plan view from the Z direction that is the direction in which the first electrode 414, the piezoelectric layer 415, and the second electrode 416 are stacked. The distance W1 between adjacent walls 418 is set to be longer than the distance W2 between adjacent active portions 413A in the X-Y plane that is a plane perpendicular to the Z direction that is the stacking direction. This makes it possible to reduce the number of walls 418 to which vibration of the vibrating plate 412 is transferred. Thus, the connection between walls 418 can be weakened, which makes it possible to suppress the generation of vibration at unwanted frequencies. Thus, it is possible to obtain a highly precise piezoelectric actuator 22.

In addition, even when the vibration of the vibrating plate 412 is transferred to the wall 418 to cause the wall 418 to vibrate, it is possible to treat the piezoelectric element 413 surrounded by the suppressing portion 43 as an isolated vibrator. Thus, it is possible to obtain a piezoelectric actuator 22 having a uniform frequency property.

Furthermore, it is possible to suppress leakage of vibration energy of the vibrating plate 412 through the wall 418. This makes it possible to enhance a quality factor of the piezoelectric element 413, which makes it possible to obtain a piezoelectric actuator 22 that is excellent in stability of vibration.

2. Second Embodiment

Next, a piezoelectric actuator 22B according to a second embodiment will be described with reference to FIGS. 10 and 11. Note that, in the following description, focus is placed on points differing from the first embodiment described above. In addition, the same reference characters are attached to the same configurations as those in the first embodiment, and explanation thereof will not be repeated.

In the piezoelectric actuator 22B according to the present embodiment, the distance W1 between a plurality of walls 418B is increased, as compared with the piezoelectric actuator 22 according to the first embodiment.

Figure 10:
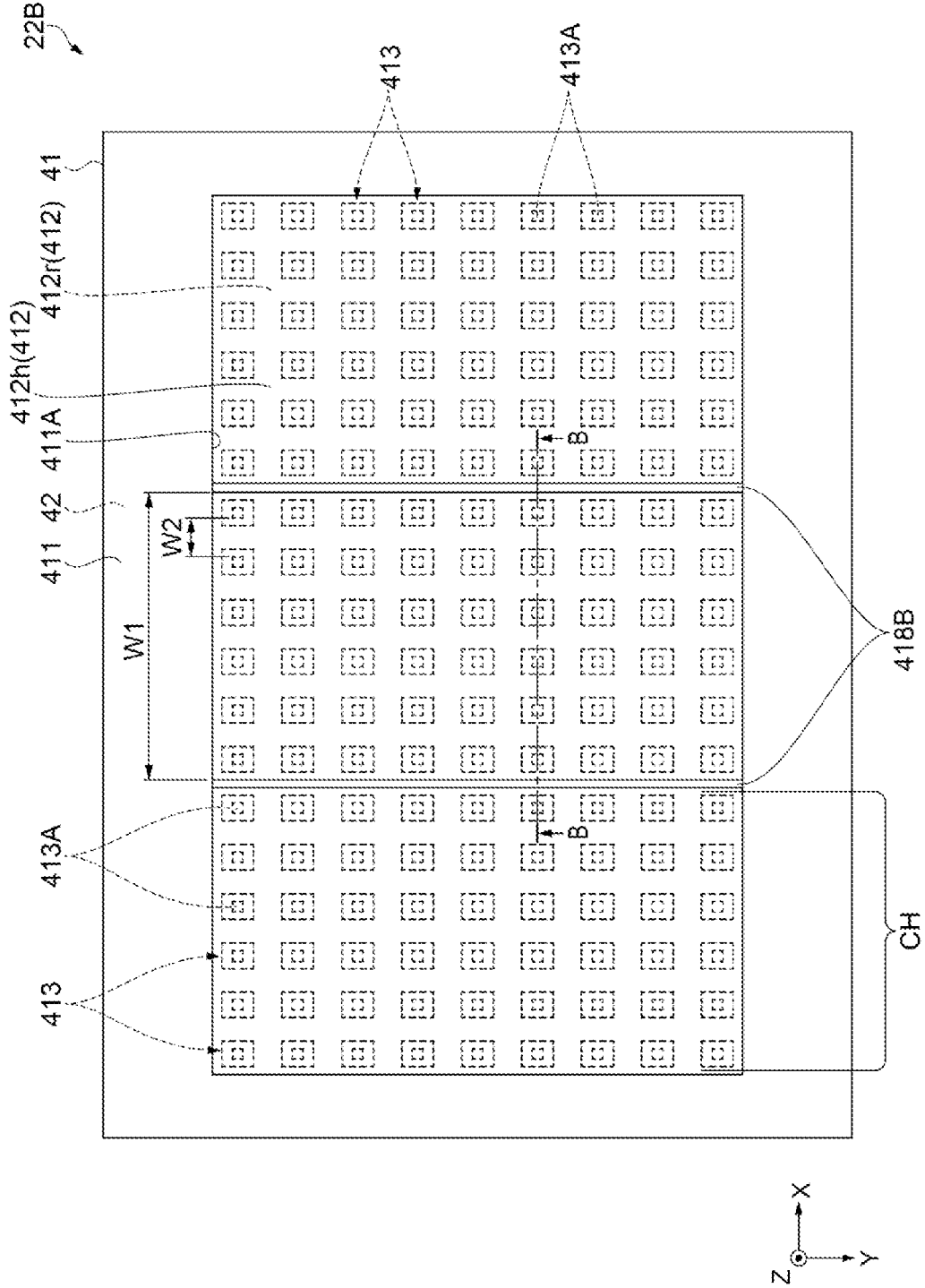
FIG. 10 is a plan view illustrating a piezoelectric actuator according to a second embodiment as viewed from a base portion side.
Figure 11:
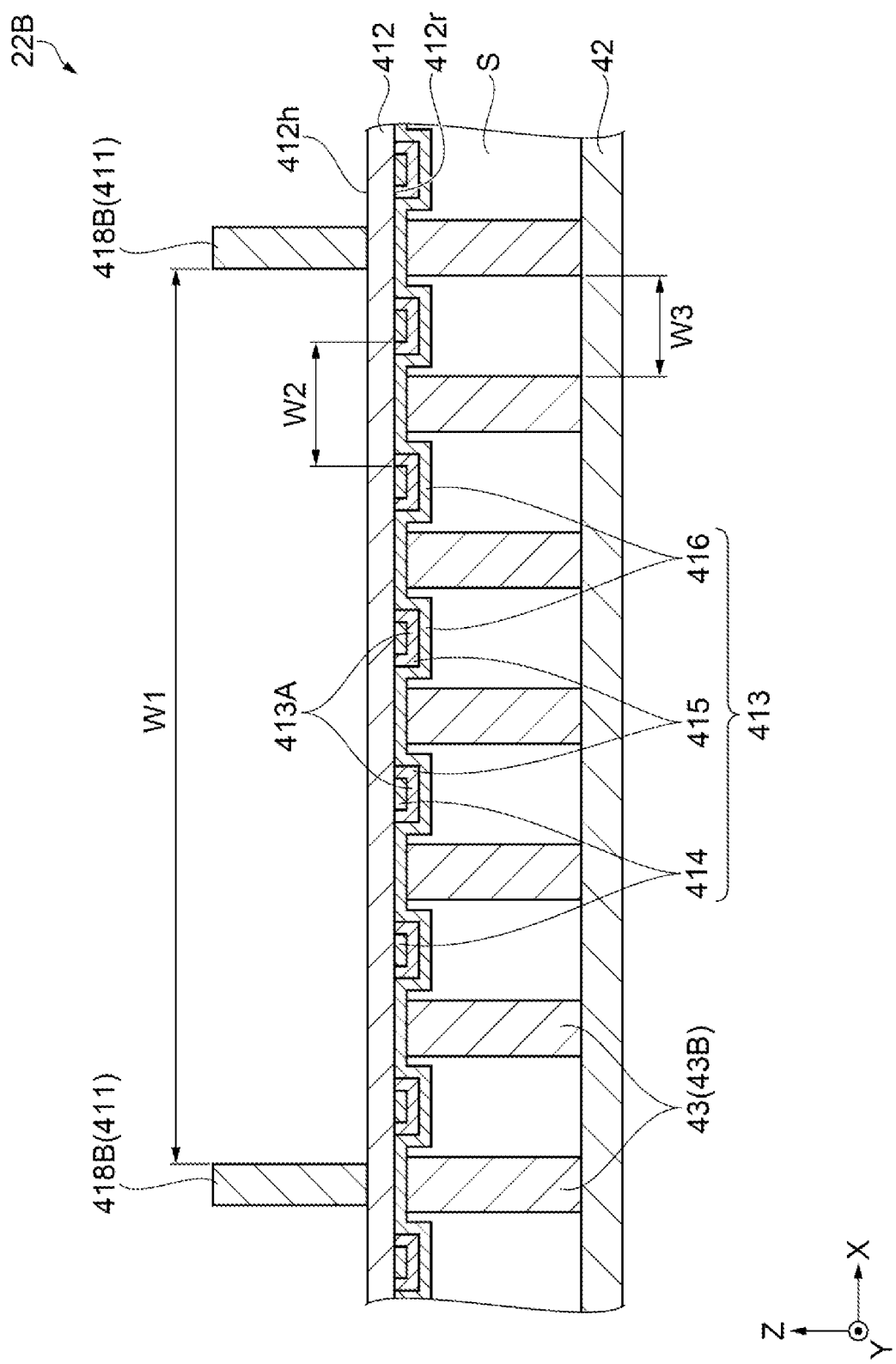
FIG. 11 is a cross-sectional view taken along the B-B line in FIG. 10.

As illustrated in FIGS. 10 and 11, the walls 418B and the active portions 413A are disposed in a manner such that the distance W1 between walls 418B disposed adjacent to each other along the X direction is longer than the distance W2 between active portions 413A of the piezoelectric element 413 disposed adjacent to each other along the X direction. Specifically, the plurality of walls 418B are provided between a plurality of channels CH disposed along the X direction in plan view from the Z direction.

In addition, in the present embodiment, six vibration regions are arranged in the X direction and between walls 418B disposed adjacent to each other along the X direction, the vibration regions being regions where the vibrating plate 412 can vibrate due to vibration of the active portion 413A without being suppressed by the suppressing portion 43.

Furthermore, in the present embodiment, a plurality of active portions 413A are disposed along the X direction and between walls 418B disposed adjacent to each other along the X direction. Specifically, six active portions 413A are disposed along the X direction and between walls 418B disposed adjacent to each other along the X direction.

With the present embodiment, it is possible to obtain the following effect in addition to the effect in the first embodiment. As compared with the piezoelectric actuator 22 according to the first embodiment, in the piezoelectric actuator 22B, the distance W1 between a plurality of walls 418B is further increased, and the number of walls 418B to which vibration of the vibrating plate 412 is transferred is further reduced. Thus, it is possible to further weaken the connection between walls 418, which makes it possible to further suppress the generation of vibration at unwanted frequencies.

What is claimed is:

1. A piezoelectric actuator, comprising:
    a substrate in which an opening is formed;
    a vibrating plate provided at the substrate and having a first surface configured to close the opening;
    a plurality of piezoelectric elements provided at a second surface correspondingly to the opening, the second surface being at an opposite side of the vibrating plate from the first surface;
    a suppressing portion provided correspondingly to the piezoelectric elements and configured to suppress vibration of the vibrating plate, and
    a plurality of walls sticking out into the opening from the first surface, wherein
    the piezoelectric elements include a first electrode, a piezoelectric layer, and a second electrode stacked in this order from a side of the second surface,
    when an active portion is a portion where the first electrode, the piezoelectric layer, and the second electrode overlap, each of the walls are provided between the active portions adjacent to each other in a plan view from a stacking direction, and
    a distance between the walls adjacent to each other is longer than a distance between the active portions adjacent to each other in a plane perpendicular to the stacking direction,
    wherein a distance between the walls adjacent to each other is at least twice a distance between suppressing portions adjacent to each other.

2. The piezoelectric actuator according to claim 1, wherein
    the suppressing portion is provided at the second surface of the vibrating plate.

3. An ultrasonic element comprising:
    the piezoelectric actuator according to claim 2;
    a transmission circuit configured to cause the piezoelectric actuator to transmit an ultrasonic wave; and
    a reception circuit configured to cause the piezoelectric actuator to receive an ultrasonic wave.

4. An ultrasonic probe comprising:
    the ultrasonic element according to claim 3; and
    a housing configured to accommodate the ultrasonic element.

5. An ultrasonic device comprising:
    the ultrasonic element according to claim 3; and
    a controller configured to control the ultrasonic element.

6. An electronic device comprising:
    the piezoelectric actuator according to claim 2.

7. An ultrasonic element comprising:
    the piezoelectric actuator according to claim 1;
    a transmission circuit configured to cause the piezoelectric actuator to transmit an ultrasonic wave; and
    a reception circuit configured to cause the piezoelectric actuator to receive an ultrasonic wave.

8. An ultrasonic probe comprising:
    the ultrasonic element according to claim 7; and
    a housing configured to accommodate the ultrasonic element.

9. An ultrasonic device comprising:
    the ultrasonic element according to claim 7; and
    a controller configured to control the ultrasonic element.

10. An electronic device comprising:
    the piezoelectric actuator according to claim 1.

* * * * *